US010611702B2

(12) United States Patent
Córdova et al.

(10) Patent No.: US 10,611,702 B2
(45) Date of Patent: Apr. 7, 2020

(54) CONVERSION OF ALCOHOLS TO LINEAR AND BRANCHED FUNCTIONALIZED ALKANES

(71) Applicant: Organofuel Sweden AB, Sundsvall (SE)

(72) Inventors: Armando Córdova, Stockholm (SE); Samson Afewerki, Uppsala (SE)

(73) Assignee: Organofuel Sweden AB, Sundsvall (SE)

( * ) Notice: Subject to any disclaimer, the term of this patent is extended or adjusted under 35 U.S.C. 154(b) by 0 days.

(21) Appl. No.: 16/325,676

(22) PCT Filed: Aug. 16, 2017

(86) PCT No.: PCT/SE2017/050826
§ 371 (c)(1),
(2) Date: Feb. 14, 2019

(87) PCT Pub. No.: WO2018/034609
PCT Pub. Date: Feb. 22, 2018

(65) Prior Publication Data
US 2019/0210940 A1   Jul. 11, 2019

Related U.S. Application Data

(60) Provisional application No. 62/375,805, filed on Aug. 16, 2016.

(51) Int. Cl.
| | | |
|---|---|---|
| C07C 45/30 | (2006.01) | |
| C07C 45/62 | (2006.01) | |
| C07B 35/02 | (2006.01) | |
| C07C 45/72 | (2006.01) | |
| C07B 31/00 | (2006.01) | |
| C07B 33/00 | (2006.01) | |
| C07D 319/06 | (2006.01) | |
| C07B 35/04 | (2006.01) | |
| C07C 45/29 | (2006.01) | |

(52) U.S. Cl.
CPC .............. *C07B 35/02* (2013.01); *C07B 31/00* (2013.01); *C07B 33/00* (2013.01); *C07B 35/04* (2013.01); *C07C 45/29* (2013.01); *C07C 45/294* (2013.01); *C07C 45/30* (2013.01); *C07C 45/62* (2013.01); *C07C 45/72* (2013.01); *C07D 319/06* (2013.01); *Y02P 20/584* (2015.11)

(58) Field of Classification Search
CPC ........ C07C 45/30; C07C 45/62; C07C 45/294
See application file for complete search history.

(56) References Cited

U.S. PATENT DOCUMENTS

| | | | | |
|---|---|---|---|---|
| 6,825,384 B1 * | 11/2004 | Prakash | ................... | C07C 45/30 568/402 |
| 7,351,867 B2 * | 4/2008 | Tanielyan | .............. | B01J 31/006 568/320 |
| 2011/0190553 A1 | 8/2011 | Onda et al. | | |

OTHER PUBLICATIONS

Nagendiran et al. Mild and Selective Catalytic Hydrogenation of the C=C Bond in alpha-beta-Unsaturated Carbonyl Compounds Using Supported Palladium Nanoparticles. Chem. Eur. Journal, vol. 22, 7184-7189. (Year: 2016).*
Verma et al. Highly dispersed palladium nanoparticles grafted into nanocrystalline starch for the oxidation of alcohols using molecular oxygen as an oxidant. Dalton Transactions, vol. 42, 11522-11527. (Year: 2013).*
Philips John R. et al: "Butanol and hexanol production in Clostridium carboxidivorans syngas fermentation: Medium development and culture techniques", (Abstract) vol. 190, Aug. 2015 pp. 114-121.
Zymochem Inc: "Carbon-conserving microbial production of 1-hexanol from bio-based feedstocks", (Abstract) Emeryville, CA; Sep. 2016.
Fernandez-Naveira, Maria C. et al: "Effect of pH control on the anaerobic H-B-E fermentation of syngas in bioreactors", (Abstract) Journal of Chemical Technology and Biotechnology; vol. 92, Issue 6 Feb. 9, 2017 pp. 1178-1185.
Dekishima Y. et al: "Extending Carbon Chain Length of 1-Butanol Pathway for 1-Hexanol Synthesis from Glucose by Engineered *Escherichia coli*", (Abstract) J. Am. Chem. Soc. 2011 Jun. 27, 2011 pp. 11399-11401.
Biermann, M. et al: "Guerbet Alcohols: From Processes under Harsh Conditions to Synthesis at Room Teperature under Ambient Pressure", (Abstract) In: ChemCatChem., Jan. 2016, vol. 8, Issue 5 pp. 895-899.
Ma J et al: "Highly Dispersed Pd on C☐ B Amorphous Alloy: Facile Synthesis via Galvanic Replacement Reaction and Synergetic Effect between Pd and Co", (Abstract) ACS Catal. Apr. 9, 2013 pp. 985-992.

(Continued)

*Primary Examiner* — Sikarl A Witherspoon
(74) *Attorney, Agent, or Firm* — Whitmyer IP Group LLC

(57) ABSTRACT

Embodiments herein concerns the eco-friendly conversion of simple alcohols to linear or branched functionalized alkanes, by integrated catalysis. The alcohols are firstlyoxidized either chemically or enzymatically to the corresponding aldehydes or ketones, followed by aldol condensations using a catalyst to give the corresponding enals or enones. The enals or enones are subsequently and selectively hydrogenated using a recyclable heterogeneous metal catalyst, organocatalyst or an enzyme to provide linear or branched functionalized alkanes with an aldehyde, keto- or alcohol functionality. The process is also iterative and can be further extended by repeating the above integrated catalysis for producing long-chain functionalized alkanes from simple alcohols.

14 Claims, No Drawings

(56) References Cited

OTHER PUBLICATIONS

Xie, Y. et al: "Highly Efficient Process for Production of Biofuel from Ethanol Catalyzed by Ruthenium Pincer Complexes", (Abstract) In: J. Am. Chem. Soc., Jul. 2016, pp. 9077-9080.
International Preliminary Report on Patentability Application No. PCT/SE2017/050826 dated Oct. 25, 2018 14 pages.
Pereira Lucas G. et al: "Production of Butanol and Other High Valued Chemicals Using Ethanol as Feedstock Integrated to a First and Second Generation Sugarcane Distillery", vol. 37, 2014 pp. 805-810.
Gabriëls, D. et al: "Review of catalytic systems and thermodynamics for the Guerbet condensation reaction and challenges for biomass valorization", In: Catal. Sci. Technol., May 2015 pp. 3876-3902.
Shimura, K. et al: "Self-coupling of secondary alcohols by Ni/CeO2 catalyst", In Appl. Catal. A. May 2013 pp. 137-142.
Witten Opinion of the International Searching Authority Application No. PCT/SE2017/050826 Completed: Nov. 1, 2017, dated Nov. 1, 2017 7 pages.
Extended European Search Report Application No. EP 1784 1760 Completed: Dec. 6, 2019; dated Dec. 13, 2019 8 pages.

* cited by examiner

CONVERSION OF ALCOHOLS TO LINEAR AND BRANCHED FUNCTIONALIZED ALKANES

TECHNICAL FIELD

Embodiments herein relate to eco-friendly and mild methods for the conversion of simple alcohols into functionalized long-chain alkanes.

BACKGROUND

Up-to-date the concern of the environment and the climate change is arguable one of our times biggest and a severe issue; hence finding new sustainable technological solutions to the replacement or reducing of fossil-based materials is a great challenge.[1] The urge and the spark in this field have promoted the scientific community to face this problem. In this context, biofuels made from renewable resources is a good alternative from the environmental point of view, having less negative impact compared to fossil based fuels. The conversion of biomass to biofuel is an intensively studied and highly attractive goal, while demanding to accomplish.[2] Alcohols such as methanol, ethanol, butanol and isopropanol are versatile organic compounds and desirable starting materials, which are easily accessible from biomass (e.g. through fermentation, pyrolysis, etc.) and can be further manipulated for the employment as biofuels.

Research in the conversion of alcohols to long-chain alkanes is starting to grow. Anbarasan et al. demonstrated the catalytic conversion of extractive fermentation to potential fuel chemicals by the integration of chemical catalysis.[4] Moreover, the group of Groger presented a mild stepwise approach for the synthesis of Guerbet alcohols.[5,6,7] It is known that aldehydes can be condensated/oligomerized using organic catalysts. However, the one-pot conversion of alcohols to oligomeric aldehydes is not known. There are examples in the use of heterogeneous catalysis for the hydrogenation or oxidation reactions of enals and allylic alcohols, respectively.[8,9] However, integrating this type of catalysis to application of short chain alcohols, aldehydes and ketones is challenging due to the elevated temperatures, needed for these applications, which are often above the boiling point of these short chain compounds. Moreover, compatibility issues may occur for less bulky substrates. Thus, the conversion of simple alcohols to valuable functional alkanes (e.g. biofuels, Guerbet alcohols, synthons) under mild conditions using integrated catalysis is of great importance.

OBJECT OF THE DISCLOSURE

It is an objective of the disclosure to synthesize long-chain linear or branched functionalized alkanes as important synthetic building blocks (synthons) or biofuel components from simple starting alcohols.

Another objective of the disclosure is to present a one-pot solution of the synthesis as described above.

Another objective of the disclosure is to synthesize long-chain linear or branched functionalized alkanes from alcohols derived from biomass or other renewable sources.

A still further objective of the disclosure is to provide methods of the aforementioned kind that is advantageous from an environmental and health standpoint.

Even more objectives will become evident from a study of the summary of the disclosure, a number of presented embodiments illustrated in the detailed description and enclosed schemes, and the appended claims.

SUMMARY

Embodiments herein are directed towards methods of producing biofuel components or valuable synthons from biomass derived alcohols or other simple alcohols. The strategy is based on the use of a multicatalytic approach by employing and combining enzyme-, organo- and heterogeneous catalysis for the conversion of simple alcohols as starting materials into products such as long-chain alcohols, long-chain saturated aldehydes or ketones, or long-chain acetals or ketals, in a sequential or one-pot procedure, according to Scheme 1.

In embodiments, methods herein may convert a starting alcohol (a simple alcohol), by:

(i) Oxidizing the starting alcohol to a corresponding aldehyde or ketone;

(ii) Condensating the corresponding aldehyde or ketone to an enal or enone; and (iii) Reducing the enal or enone to a product, said product being an alcohol, an aldehyde, a ketone, an acetal or a ketal having a longer chain than the chain of the starting alcohol.

Scheme 1 - Iterative integrated catalysis strategy for the conversion of simple alcohols to higher value functional alkanes.

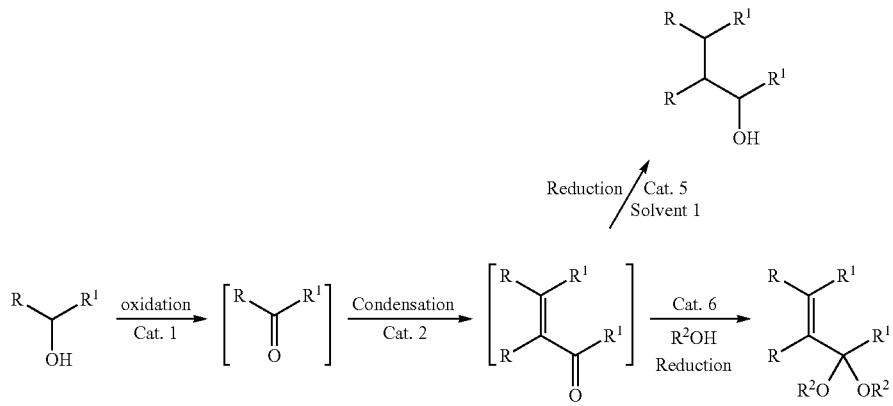

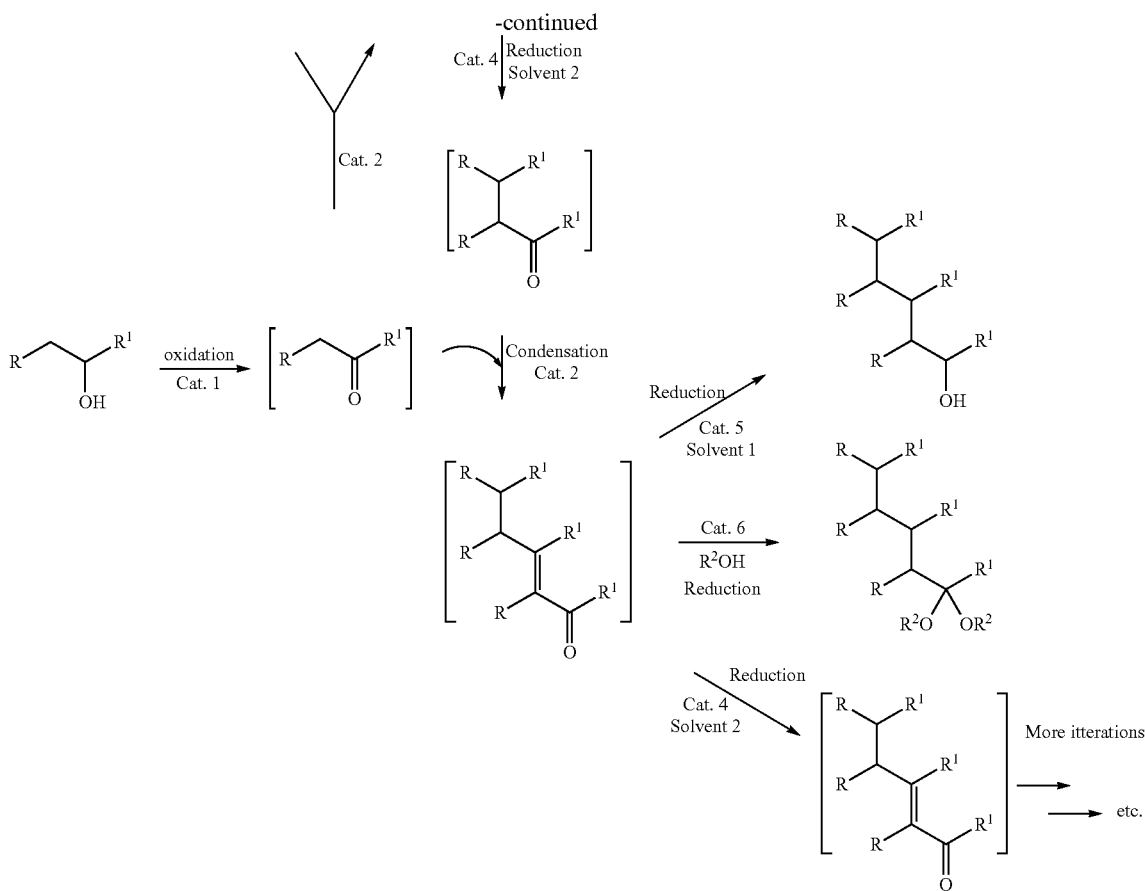

By simple alcohols, it is understood herein, easily available, mono-, or dialcohols, having a linear or branched, saturated or unsaturated carbon chain of between 1 and 30 carbon atoms (C1-30). By long-chain functionalized alkanes (or products) it is understood herein a compound having a carbon chain longer than the carbon chain of the starting material from which the said product was generated.

Suitable alcohols that may be used for the oxidation step of methods herein are $RCH_2OH$ or $RCH(OH)R^1$, wherein R is H, alkyl, aryl, alkenyl, or heterocyclic group and $R^1$ is alkyl.

In another embodiment, as shown even in scheme 1, the method of embodiments herein may be applied iteratively, wherein the steps of methods described above may be repeated on a product alcohol, which used as a starting alcohol is converted to a product with even longer chain.

In methods herein, a suitable oxidant may be chosen, depending on the nature of the starting alcohol. The oxidant may be oxygen, air, hydrogen peroxide, or sodium hypochlorite. A person skilled in the art may determine the nature of the oxidant for the specific starting alcohol.

An oxidizing catalyst may be employed in the oxidizing step. Suitable catalysts, depending on the nature of the starting alcohol, may be a heterogeneous supported metal catalyst, a homogeneous organometallic complex, a metal-free catalyst, or an enzyme. A person skilled in the art may determine the nature of the catalyst for the specific starting alcohol.

A suitable metal-free condensation catalyst or a salt thereof may be used for the condensation of the corresponding aldehyde or ketone into the enal or enone.

In the reduction step of methods herein, a suitable reduction agent (such as formic acid, $H_2$, ammonium formiate, or Hantzsch ester) may be optionally combined with a suitable heterogeneous or homogenous metal catalyst, a metal-free catalyst, or an enzyme, converting the enal or enone into the product.

When the method is performed in one-pot fashion, multi-catalytic cascade relay sequences are involved, combining enzymatic, organo- and heterogeneous catalysis of the three steps as described above. The advantages of one-pot synthesis are well known, as they require considerably less time and energy to perform, and generate often less by-products.

Alcohols that can be converted into the corresponding aldehydes or ketones by using methods herein may be for example methanol, ethanol, propanol, butanol, benzyl alcohol, isopropanol, hexanol, octanol, nonanol, hexadecanon and octadecanol 1. Aldehydes that can be converted to enals or enones by using methods herein may be for example acetaldehyde, formaldehyde, propanal, butanal, pentanal, hexanal, octanal 2,4-Hexadienal, cinnamic aldehyde, or benzyl aldehyde.

The starting alcohol, may have been obtained from renewable resources, such as biomass, triglycerides, wood, algae, syngas, or may be generated through fermentation or pyrolysis. The starting alcohol may be a fatty alcohol. Relaying on renewable sources for providing the starting material, decreases the impact of the method on the environment.

In alternative embodiments, methods herein may comprise:
(i) providing the starting alcohol,
(ii) providing an oxidant, such as air, $O_2$, or NaClO,
(iii) optionally providing an oxidation catalysts system such as TEMPO, CuBr, bpy, NMI, $O_2$; or TEMPO, $HNO_3$, HCl, $O_2$; or TEMPO, NaOCl, KBr; or a heterogeneous supported metal catalyst (Pd, Ag, Ru, Ir, Fe); or a homogeneous catalyst system (Pd, Ag, Ru, Ir, Fe) and converting the starting alcohol in the presence of said oxidation catalyst system into the corresponding aldehyde or ketone,
(iv) providing an amine catalyst system or a salt thereof,
(v) optionally including an acid, and converting the corresponding aldehyde or ketone, in the presence of said amine catalyst system or the salt thereof, optionally including an acid, into the enal or enone,
(vi) providing a reducing agent, such as formic acid, $H_2$, or ammonium formiate,
(vii) optionally providing a reducing catalyst, such as a heterogeneous supported metal catalyst (Pd, Ag, Ru, Ir, Fe, Ni, or Co), or a homogeneous organometallic complex (Pd, Ag, Ru, Ir, Fe, Ni, or Co); and reducing the enal or enone, optionally in the presence of said reducing catalyst, into the product.

DETAILED DESCRIPTION

Embodiments herein relate to environmentally and very mild processes for the conversion of simple alcohols to advanced biofuel compounds or synthons (Scheme 1). The synthetic strategy starts with the selective oxidation of the alcohols either chemically or enzymatically to the corresponding aldehydes or ketones, respectively. Furthermore, in the next step the aldehydes or ketones are condensated to long-chain unsaturated compounds (enals or enones) by the aid of a suitable catalyst (e.g. an organocatalyst or a salt thereof). The enal or enone is then selectively hydrogenated in the presence of a heterogeneous metal catalyst and a suitable reducing agent (such as hydrogen gas, ammonium formiate, formic acid) or through enzymatic reduction, providing saturated aldehyde, keto- or alcohol functionalized alkanes. Notable, the steps can be integrated in one-pot or in sequential proceedure, taking the chemical process towards a more sustainable, time, economic and energy efficient approach.[3] The sequences can also be repeated in an iterative fashion so that the carbon chains of the product can be further extended (Scheme 1).

In Example 1 and Table 1 below, the results from the study of the oxidation step are summarized. Among the oxidizing systems tested with oxygen as oxydizer, the combination TEMPO ((2,2,6,6-Tetramethylpiperidin-1-yl)oxyl), NaOCl and NaBr gives highest yield and shorter reaction time, at a temperature as mild as of 10° C. This illustrates the importance and efficiency of choosing a suitable catalyst system for the oxidation of a given starting alcohol.

The conversion of the aldehyde into corresponding enal by condensation or oligomerization can be achieved with a suitable organocatalyst or a salt thereof, for instance pyrrolidine, proline, ammonium fluoride, ammonium formiate or glycine. In some cases, acid may be used as additive, as for example acetic acid. (See Example 2 and Table 2) For reaching the desired selectivity (with the enal 2 as major or only condensation product), the choice of catalyst is essential.

The conversion of the unsaturated long-chain linear or branched compound (enal or enone) to the corresponding saturated long-chain linear or branched product by hydrogenation/reduction was studied in Example 3, and summarized in Table 3. A heterogeneous Pd-catalyst in the presence of $H_2$-gas, and a hydrogenating enzyme or an organocatalyst proved to be suitable reduction system for the studied reaction.

The learnings from the isolated reactions discussed above, were applied to a one-pot conversion method according to embodiments herein, comprising the condensation and the reduction steps. (See example 4, and Table 4). The compatibility of the two reactions performed in a one-pot fashion and implicitly the compatibility and stability of the two catalyst systems was proven by the high conversion and selectivity observed with a variety of different starting alcohols. Moreover, the stability of the Pd-catalyst as reduction catalyst is proven by a 5-recycle study (See Example 5 and Table 5), which opens for an ecologic approach where the metal catalyst may be recycled.

The one-pot reaction system was tested as well for the iterative approach, where the product generated through the conversion of a stating alcohol or aldehyde according to embodiments herein, was used as starting material in methods described herein. (as described in Scheme 3, Example 6), More one-pot examples of conversion of different alcohols into the corresponding aldehydes, followed by condensation to enals and subsequent reduction to the saturated, branched products are illustrated in Examples 7 and 8, proving the wide scope of methods herein.

Starting from simple alcohols and combining in one-pot metal or metal-free oxidation, or alternatively enzymatic oxidation step, with organocatalytic condensation step and finally with heterogeneous metal catalyzed, organocatalytic or enzymatic hydrogenation step gives, in a selective manner and with excellent yields, the product (being an alcohol, an aldehyde or a ketone, an enal or enone) with a longer chain than the chain of the starting alcohol.

Embodiments herein may utilize a renewable source as a source of ethanol and other simple alcohols, the said source being biomass, triglycerides, wood, algae, or syngas (preferably generated in a gasification process). Moreover, embodiments herein may be performed in one-pot without any purification of intermediates. The use of renewable sources of starting materials, an organocatalyst, an enzyme and a recyclable heterogeneous metal catalyst, in a one-pot synthesis, renders embodiments herein sustainable and environmentally benign.

The process may be started from readily available, simple aldehydes or ketones, without the need of a first oxidation step.

EXAMPLES

General Methods $^1$H NMR spectra were recorded on a Bruker Avance (500 MHz or 400 MHz) spectrometer. Chemical shifts are reported in ppm from tetramethylsilane with the solvent resonance resulting from incomplete deuterium incorporation as the internal standard (CDCl$_3$: □7.26 ppm). Data are reported as follows: chemical shift, multiplicity (s=singlet, d=doublet, q=quartet, br=broad, m=multiplet), and coupling constants (Hz), integration. $^{13}$C NMR spectra were recorded on a Bruker Avance (125.8 MHz or 100 MHz) spectrometer with complete proton decoupling; Chemical shifts are reported in ppm from tetramethylsilane with the solvent resonance as the internal standard (CDCl$_3$: □77.16 ppm).

Commercial reagents were used as purchased without any further purification. Aluminum sheet silica gel plates (Fluka 60 F254) were used for thin-layer chromatography (TLC), and the compounds were visualized by irradiation with UV light (254 nm), or by treatment with a solution of phosphomolybdic acid (25 g), Ce(SO$_4$)$_2$.H$_2$O (10 g), conc. H$_2$SO$_4$ (60 mL), and H$_2$O (940 mL), followed by heating or by dipping in KMnO$_4$-Stain followed by heating or washing away the stain with water. Purification of the product was carried out by flash column chromatography using silica gel (Fluka 60, particle size 0.040-0.063 mm)

Example 1—Optimization Studies of the Oxidation Step (Table 1)

To a microwave-vial containing hexanol (102 mg, 1 mmol, 1 equiv.) was added the oxidation system and solvent shown in table 1 and afterwards the reaction mixture was stirred at the temperature and for the time stated in table 1.

TABLE 1

Optimization studies of the oxidation

| Entry | Tempo (%) | Additives | Solvent | Temp. (° C.) | Time (h) | Conv. (%)[a] |
|---|---|---|---|---|---|---|
| 1 | 1 | NaOCl (1.6M), NaBr (10 mol %) NaHCO$_3$ (0.53M) | CH$_2$Cl$_2$/H$_2$O | 5 | 18 | 8 |
| 2[b] | 10 | NaOCl (1.6M), KBr (10 mol %) NaOH (2M) | CH$_2$Cl$_2$/H$_2$O | 5 | 21 | 20 |
| 3 | 5 | HNO$_3$ (10 mol %) HCl (10 mol %) | CH$_3$CN/H$_2$O | 45 | 24 | 20 |
| 4 | 5 | CuBr (5 mol %), bpy (5 mol %) NMI (10 mol %) | CH$_3$CN | 24 | 24 | 73 |
| 5[c] | 5 | CuBr (5 mol %), bpy (5 mol %) NMI (10 mol %) | CH$_3$CN | 24 | 45 | 83 |
| 6 | — | MCF-AmP—Pd(0) (1.5 mol %) | p-Xylene | 110 | 24 | 14 |
| 7[b] | 1 | NaOCl (1.6M) NaBr (10 mol %) | CH$_2$Cl$_2$/H$_2$O | 10 | 10/60 | >99 |
| 8[b] | 1 | NaOCl (1.6M), NaBr (10 mol %) | Toluene/H$_2$O | 10 | 6 | 91 |
| 9[b] | 1 | NaOCl (1.6M), NaBr (10 mol %) | Toluene/H$_2$O | 10 | 1 | >99 |
| 10[b,d] | 1 | NaOCl (1.6M), NaBr (10 mol %) | CH$_2$Cl$_2$/H$_2$O | 10 | 3 | 82 |
| 11[c,d] | 1 | NaOCl (1.6M), NaBr (10 mol %) | CH$_2$Cl$_2$/H$_2$O | 10 | 10/60 | >99 |

[a]Determined by $^1$H NMR spectroscopy on the crude reaction mixture using mesitylene as internal standard. [b]Sat. NaHCO$_3$ was used to adjust the pH to 9 of NaOCl. [c]The reaction was performed with octanol. [d]The reaction was performed with ethanol.

Example 2—Optimization Studies of the Condensation Step (Table 2)

To a microwave-vial containing acetaldehyde (88.1 mg, 2 mmol, 1 equiv.) was added the oligomerization catalyst and solvent shown in table 2 and afterwards the reaction mixture was stirred at room temperature for the time stated in table 2.

TABLE 2

Optimization of the organocatalytic condensation/oligomerization

| Entry | Catalyst (mol %) | Solvent | Time (h) | Conv.[a] | Ratio[a] 2:3:4 |
|---|---|---|---|---|---|
| 1[b] | Pyrrolidine/HOAc (0.3) | — | 168 | 20 | 47:11:41 |
| 2[c] | Proline (1.0) | Toluene | 14 | 29 | 80:7:13 |
| 3[c] | Pyrrolidine/HOAc (5.0) | Toluene | 3 | 95 | 80:20:0 |
| 4[b] | Pyrrolidine/HOAc (5.0) | — | 72 | 93 | 26:46:28 |
| 5[d] | NH$_4$F (30.0) | water | 168 | 12 | 100:0:0 |
| 6[d] | HCO$_2$NH$_4$ (30.0) | water | 168 | 12 | 100:0:0 |
| 7[d] | Glycine (20.0) | water | 168 | 12 | 100:0:0 |
| 8[e] | Pyrrolidine/HOAc (5.0) | Toluene | 1.5 | 96 | 59:41:0 |
| 9[c] | Pyrrolidine/HOAc (5.0) | Toluene/water | 30 | 92 | 87:8:5 |
| 10[c] | Pyrrolidine/HOAc (5.0) | water | 30 | 20 | 62:0:38 |
| 11[c] | Pyrrolidine/HOAc (5.0) | brine | 30 | 13 | 74:0:26 |
| 12[c] | Pyrrolidine/HOAc (5.0) | CH$_2$Cl$_2$/water | 3 | >99 | 74:26:0 |

[a]Determined by $^1$H NMR spectroscopy on the crude reaction mixture using mesitylene as internal standard. [b]The reaction was performed in the presence of water (100 μL). [c]The concentration of acetaldehyde is 4M. [d]The concentration of acetaldehyde is 1M. The temperature was increase to 37° C. after 48 h. [e]The concentration of acetaldehyde is 2M and the reaction was performed at 60° C.

Example 3—The Pd-Catalyst Hydrogenation Step (Table 3)

In a microwave vial containing trans, trans-2, 4 hexadienal (9.6 mg, 0.1 mmol) in solvent (1 mL) was added MCF-AmP-Pd(0) (6.5 mg, 5 mol %) or CPG (25 mg, 5 mol %) or Pd/C (5.3 mg, 5 mol %, 10 Wt. %) and a balloon filled with $H_2$-gas was connected to the vial and stirred for 3 h in room temperature.

TABLE 3

Studies of the heterogeneous Pd-catalyst hydrogenation

| Entry | Pd-catalyst | Solvent | Conv. (%)[a] |
|---|---|---|---|
| 1 | MCF-AmP—Pd(0) | Toluene | >99 |
| 2 | CPG-Pd(0) | Toluene | >99 |
| 3 | Pd/C | Toluene | >99 |
| 4 | Pd/C | Water | >99 |
| 5 | MCF-AmP—Pd(0) | Water | >99 |
| 6 | MCF-AmP—Pd(0) | Acetonitrile | >99 |
| 7 | MCF-AmP—Pd(0) | MeOH[b] | >99 |

[a]Determined by $^1$H NMR spectroscopy on the crude reaction mixture using mesitylene as internal standard. [b]The methanol in situ generated acetal of hexanal (1,1-dimethoxyhexane) was formed as the product.

Example 4—Substrate Scope for the One-Pot Condensation and Hydrogenation (Table 4)

In a dried microwave vial containing the aldehyde (2 mmol, 1 equiv.) in toluene (1 mL), was added pyrrolidine (7.1 mg, 0.1 mmol, 5 mol %) and acetic acid (6.0 mg, 0.1 mmol, 5 mol %). Then the mixture was stirred in 60° C. for the time stated in table 4. Then MCF-AmP-Pd(0) (130 mg, 5 mol %) was added followed by connection of a balloon filled with $H_2$-gas and the reaction stirred at room temperature for 3 h.

Example 5—Recycling Studies of the MCF-AmP-Pd(0)-Catalyst for the Hydrogenation Reaction (Table 5)

In a microwave vial containing 2-ethyl hexenal (9.6 mg, 0.1 mmol) in toluene (1 mL) was added MCF-AmP-Pd(0) (6.5 mg, 5 mol %) and a balloon filled with $H_2$-gas was connected to the vial and stirred for 3 h at room temperature. Afterwards the reaction mixture was centrifuged and the solid heterogeneous catalyst was further washed with dichloromethane three times by centrifugation and the dried under overnight under vacuum. Then the dried and recycled MCF-AmP-Pd(0) was further used in the next cycle.

TABLE 5

Recycling studies of the MCF-AmP—Pd(0)-catalyzed hydrogenation

| Cycle | Conv. (%)[a] |
|---|---|
| 1 | >99 |
| 2 | >99 |
| 3 | >99 |
| 4 | >99 |
| 5 | >99 |

[a]Determined by $^1$H NMR spectroscopy on the crude reaction mixture using mesitylene as internal standard.

Example 6—One-Pot Reaction from Acetaldehyde to 2-Ethyl-Hexanal (Scheme 3)

In a dried microwave vial containing acetaldehyde (88.1 mg, 2 mmol) in toluene (1 mL), was added pyrrolidine (7.1 mg, 0.1 mmol, 5 mol %) and acetic acid (6.0 mg, 0.1 mmol, 5 mol %). Then the mixture was stirred in 60° C. for 1.5 h. Then MCF-AmP-Pd(0) (134 mg, 5 mol %) or Pd/C (106 mg, 5 mol %) was added followed by connection of a balloon filled with $H_2$-gas and the reaction stirred at room temperature for 3 h. Then $H_2$ gas was removed and pyrrolidine (7.1

TABLE 4

Substrate scope for the one-pot condensation and hydrogenation

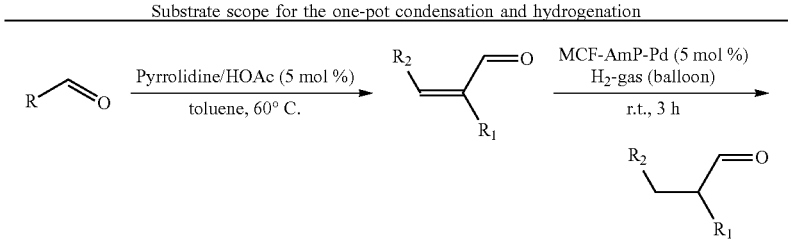

| Entry | R | $R_1$ | $R_2$ | Time (h) | Conv. (%)[a] |
|---|---|---|---|---|---|
| 1 | $CH_3$ | H | $CH_3$ | 1.5 | 96 |
| 2[b] | $C_3H_7$ | $C_2H_5$ | $C_3H_7$ | 72 | 93 |
| 3 | $C_3H_7$ | $C_2H_5$ | $C_3H_7$ | 4 h | >99 |
| 4 | $C_5H_{11}$ | $C_4H_9$ | $C_5H_{11}$ | 4 h | 97 |
| 5 | $BnCH_2$ | Bn | $BnCH_2$ | 4 h | >99 |

[a]Determined by $^1$H NMR spectroscopy on the crude reaction mixture using mesitylene as internal standard. The conversion is given for the oligomerization step. In the hydrogenation step >99% conversion was obtained in all examples. [b]The reaction was performed at 25° C.

mg, 0.1 mmol, 5 mol %) and acetic acid (6.0 mg, 0.1 mmol, 5 mol %) were added and the reaction mixture was stirred at 60° C. for 8 h. Subsequently, the balloon filled with H$_2$-gas was connected and the reaction kept stirring at room temperature for 6 h.

Scheme 3 - One-pot reaction from acetaldehyde to 2-ethyl-hexanal

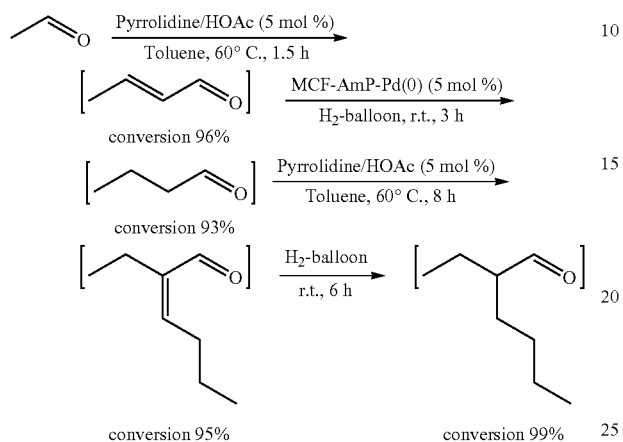

Example 7—One-Pot Multicatalytic Strategy for the Synthesis of Saturated Branched Compound Starting from Hexanol (Scheme 4 and 5)

To a microwave-vial containing hexanol (120 mg, 1 mmol, 1 equiv.) or octanol (130 mg, 1 mmol, 1 equiv.) and Tempo (1.6 mg, 0.01 mmol, 1 mol %) was added CH$_2$Cl$_2$ (2.5 mL) and the reaction mixture was sonicated for 3 minutes. Afterwards the reaction was cooled to 10° C. and stirred vigorously. Subsequently, cooled NaBr (0.1 M, 0.1 mL, 10 mol %) and NaOCl (1.6 M, 2.8 equiv. pH adjusted to 9 by sat. NaHCO$_3$) were added. Afterwards a balloon filled with O$_2$-gas was connected and the reaction stirred at 10° C. for 10 min. Then the organic phase was extracted by using CH$_2$Cl$_2$ (3×5 mL) and dried over Na$_2$SO$_4$. Afterwards the solvent was evaporated and the dry reaction mixture was transferred to a microwave-vial by toluene (o.5 mL) and then pyrrolidine (3.4 mg, 0.1 mmol, 5 mol %) and acetic acid (6.0 mg, 0.1 mmol, 5 mol %) were added and the reaction mixture was stirred at 60° C. for 4 h. Then the reaction was cooled to room temperature and subsequently, MCF—AmP-Pd(0) (67 mg, 5 mol %) was added followed by connection of a balloon filled with H$_2$-gas and the reaction stirred at room temperature for 4 h.

Scheme 4 - One-pot multicatalytic reaction for the synthesis of saturated branched compound starting from hexanol

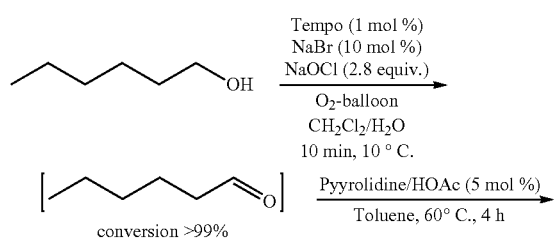

Scheme 5 - One-pot multicatalytic reaction for the synthesis of saturated branched compound starting from octanol

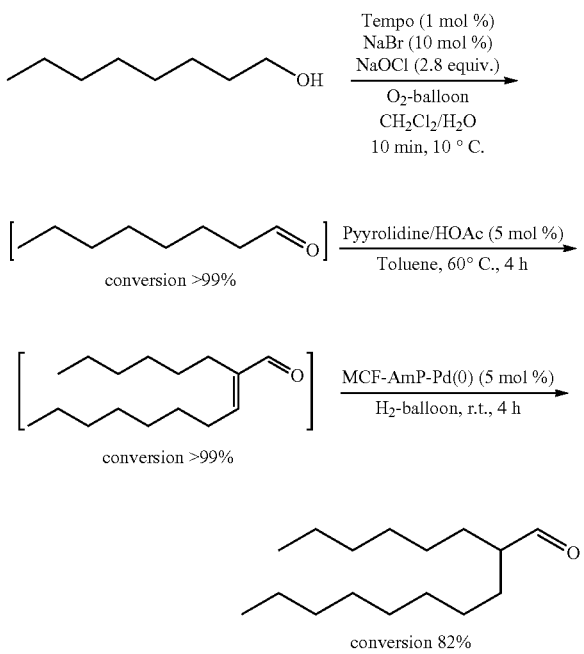

Example 8—One-Pot Multicatalytic Strategy for the Synthesis of Butyraldehyde Starting from Ethanol (Scheme 6)

To a microwave-vial containing ethanol (46 mg, 1 mmol, 1 equiv.) and Tempo (1.6 mg, 0.01 mmol, 1 mol %) was added CH$_2$Cl$_2$ (2.5 mL) and the reaction mixture was sonicated for 3 minutes. Afterwards the reaction was cooled to 10° C. and stirred vigorously. Subsequently, cooled NaBr (0.1 M, 0.1 mL, 10 mol %) and NaOCl (1.6 M, 2.8 equiv. pH adjusted to 9 by sat. NaHCO$_3$) were added. Afterwards a balloon filled with O$_2$-gas was connected and the reaction stirred at 10° C. for 3 h. Afterwards pyrrolidine (3.4 mg, 0.05 mmol, 5 mol %) and acetic acid (3.0 mg, 0.05 mmol, 5 mol %) were added and the reaction mixture was stirred at room temperature for 3 h. Then the reaction was cooled to room temperature and subsequently, MCF-AmP-Pd(0) (67 mg, 5 mol %) was added followed by connection of a balloon filled with H$_2$-gas and the reaction stirred at room temperature for 3 h.

Scheme 6 - One-pot multicatalytic reaction for the synthesis of butyraldehyde compound starting from ethanol

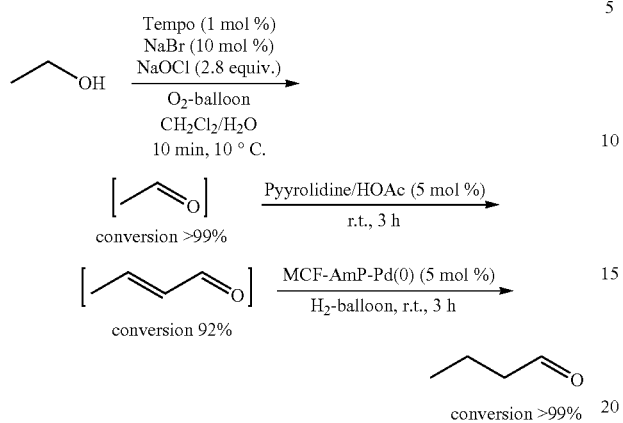

Structures of the analyzed intermediates and products:

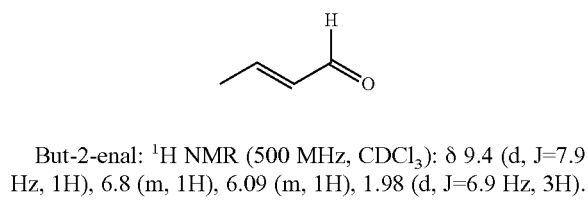

But-2-enal: ¹H NMR (500 MHz, CDCl₃): δ 9.4 (d, J=7.9 Hz, 1H), 6.8 (m, 1H), 6.09 (m, 1H), 1.98 (d, J=6.9 Hz, 3H).

2-ethylhex-2-enal: ¹H NMR (500 MHz, CDCl₃): δ 9.39 (s, 1H), 6.43 (t, J=7.6 Hz, 1H), 2.4 (m, 4H), 1.57 (m, 2H), 1.01 (t, J=7.5 Hz, 6H).

2-ethylhexanal: ¹H NMR (500 MHz, CDCl₃): δ 9.6 (d, J=3 Hz, 1H), 2.2 (m, 1H), 1.67 (m, 2H), 1.51 (m, 2H), 1.33 (m, 4H), 0.95 (t, J=7.3 Hz, 6H).

2-butyloct-2-enal: ¹H NMR (500 MHz, CDCl₃): δ 9.39 (s, 1H), 6.44 (t, J=7.5 Hz, 1H), 2.28 (t, J=7.1 Hz, 2H), 1.53 (m, 2H), 1.37 (m, 10H), 0.95 (m, 6H).

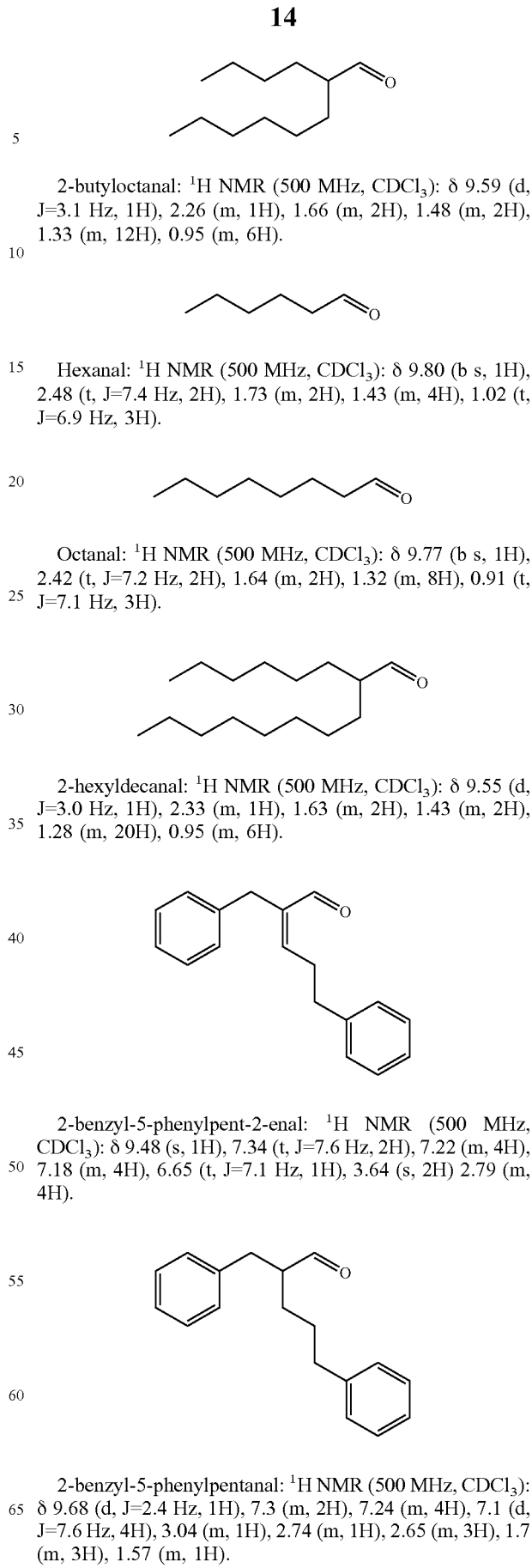

2-butyloctanal: ¹H NMR (500 MHz, CDCl₃): δ 9.59 (d, J=3.1 Hz, 1H), 2.26 (m, 1H), 1.66 (m, 2H), 1.48 (m, 2H), 1.33 (m, 12H), 0.95 (m, 6H).

Hexanal: ¹H NMR (500 MHz, CDCl₃): δ 9.80 (b s, 1H), 2.48 (t, J=7.4 Hz, 2H), 1.73 (m, 2H), 1.43 (m, 4H), 1.02 (t, J=6.9 Hz, 3H).

Octanal: ¹H NMR (500 MHz, CDCl₃): δ 9.77 (b s, 1H), 2.42 (t, J=7.2 Hz, 2H), 1.64 (m, 2H), 1.32 (m, 8H), 0.91 (t, J=7.1 Hz, 3H).

2-hexyldecanal: ¹H NMR (500 MHz, CDCl₃): δ 9.55 (d, J=3.0 Hz, 1H), 2.33 (m, 1H), 1.63 (m, 2H), 1.43 (m, 2H), 1.28 (m, 20H), 0.95 (m, 6H).

2-benzyl-5-phenylpent-2-enal: ¹H NMR (500 MHz, CDCl₃): δ 9.48 (s, 1H), 7.34 (t, J=7.6 Hz, 2H), 7.22 (m, 4H), 7.18 (m, 4H), 6.65 (t, J=7.1 Hz, 1H), 3.64 (s, 2H) 2.79 (m, 4H).

2-benzyl-5-phenylpentanal: ¹H NMR (500 MHz, CDCl₃): δ 9.68 (d, J=2.4 Hz, 1H), 7.3 (m, 2H), 7.24 (m, 4H), 7.1 (d, J=7.6 Hz, 4H), 3.04 (m, 1H), 2.74 (m, 1H), 2.65 (m, 3H), 1.7 (m, 3H), 1.57 (m, 1H).

REFERENCES

1. Robbins, M. Fuelling politics. *Nature*, 2011, 474, 22-24.
2. Demirbas, A. Competitive liquid biofuels from biomass. *Appl. Energy* 2011, 88, 17-28.
3. Anastas, P. T.; Warner, J. C. *Green Chemistry: Theory and Practice*, Oxford University Press (2000).
4. Anbarasan, P. et al. Integration of chemical catalysis with extractive fermentation to produce fuels. *Nature*, 2012, 491, 235-239.
5. Biermann, M.; Gruβ, H.; Hummel, W.; Gröger, H. Guerbet Alcohols: From Processes under Harsh Conditions to Synthesis at Room Temperature under Ambient Pressure. *Chem-CatChem* 2016, 8, 895-899.
6. Kusumoto, S.; Ito, S.; Nozaki, K. Direct Aldol Polymerization of Acetaldehyde with Organocatalyst/Brønsted Acid System. *Asian J. Org. Chem.* 2013, 2, 977-982.
7. Noziére, B.; Dziedzic, P.; Córdova, A. Inorganic ammonium salts and carbonate salts are efficient catalysts for aldol condensation in atmospheric aerosols. Phys. Chem. Chem. Phys. 2010, 12, 3864-3872.
8. Deiana, L. et al. Combined Heterogeneous Metal/Chiral Amine: Multiple Relay Catalysis for Versatile Eco-Friendly Synthesis. *Angew. Chem. Int. Ed.* 2014, 53, 3447-3451.
9. Deiana, L.; Ghisu, L.; Córdova, O.; Afewerki, S.; Zhang, R.; Córdova, A. Efficient and Highly Enantioselective Aerobic Oxidation-Michael-Carbocyclization Cascade Transformations by Integrated Pd(0)-CPG Nanoparticles/Chiral Amine Relay Catalysis. *Synthesis*, 2014, 46, 1303-1310.

Embodiments herein may be defined by the following clauses:

1. A method for the conversion of alcohols comprising either
   (ia) providing an aldehyde; and (iia) bringing said aldehyde to a longer-chain enal; and (iiia) bring said enal to an aldehyde.
   or (ib) providing an aldehyde; and (iib) bringing said aldehyde to a longer-chain enal; and (iiib) bring said enal to an alcohol.
   or (ic) providing a ketone; and (iic) bringing said ketone to a longer-chain enone; and (iiic) bring said enone to a ketone.
   or (id) providing a ketone; and (iid) bringing said ketone to a longer-chain enone; and (iiid) bring said enone to an alcohol.
   or (ie) providing an aldehyde; and (iie) bringing said aldehyde to a longer-chain enone; and (iiie) bring said enone to a ketone.
   or (if) providing an aldehyde; and (iif) bringing said aldehyde to a longer-chain enone; and (iiif) bring said enone to an alcohol.
   or (ig) providing an aldehyde; and (iig) bringing said aldehyde to a longer-chain enal; and (iiig) bring said enal to an acetal.
   or (ih) providing a ketone; and (iih) bringing said ketone to a longer-chain enone; and (iiic) bring said enone to an acetal.
2. The method according to clause 1 wherein said alcohol-groups are primary alcohols, said aldehydes moiety have an R group (R=H, alkyl, aryl, heterocyclic and alkenes), said longer-chain enals have R groups (R=H, alkyl, aryl, heterocyclic and alkenes), said aldehydes have R (R=H, alkyl, aryl, heterocyclic and alkenes) groups.
3. The method according to clause 1 wherein said alcohol-groups are primary alcohols, said aldehydes moiety have an R group (R=H, alkyl, aryl, heterocyclic and alkenes), said longer-chain enals have R groups (R=H, alkyl, aryl, heterocyclic and alkenes), said alcohols have R (R=H, alkyl, aryl, heterocyclic and alkenes) groups.
4. The method according to clauses 1-3 where said primary alcohol and aldehyde groups were generated via the sequence described in claim 1-3.
5. The method according to clause 1 wherein said alcohol-groups are secondary alcohols, said keto-group have R (R=H, alkyl, aryl, heterocyclic and alkenes) and $R^1$ ($R^1$=methyl, ethyl, alkyl) groups, said longer-chain enones have R (R=H, alkyl, aryl, heterocyclic and alkenes) and $R^1$ ($R^1$=methyl, ethyl, alkyl) groups, said ketones have R (R=H, alkyl, aryl, heterocyclic and alkenes) and $R^1$ ($R^1$=methyl, ethyl, alkyl) groups.
6. The method according to clause 1 wherein said alcohol-groups are secondary alcohols, said keto-group have R (R=H, alkyl, aryl, heterocyclic and alkenes) and $R^1$ ($R^1$=methyl, ethyl, alkyl) groups, said longer-chain enones have R (R=H, alkyl, aryl, heterocyclic and alkenes) and $R^1$ ($R^1$=methyl, ethyl, alkyl) groups, said alcohols have R (R=H, alkyl, aryl, heterocyclic and alkenes) and $R^1$ ($R^1$=methyl, ethyl, alkyl) groups.
7. The method according to clauses 1, 5-6 where said secondary alcohol and keto groups were generated via the sequence described in claims 1, 5 and 6.
8. The method according to clause 1 wherein said alcohol-groups are primary alcohols, said aldehydes moiety have an R group (R=H, alkyl, aryl, heterocyclic and alkenes), said longer-chain enals have R groups (R=H, alkyl, aryl, heterocyclic and alkenes), said acetals have R (R=H, alkyl, aryl, heterocyclic and alkenes) groups and $R^2$ ($R^2$=methyl, ethyl, alkyl) groups.
9. The method according to clause 1 wherein said alcohol-groups are secondary alcohols, said keto-group have R (R=H, alkyl, aryl, heterocyclic and alkenes) and $R^1$ ($R^1$=methyl, ethyl, alkyl) groups, said longer-chain enones have R (R=H, alkyl, aryl, heterocyclic and alkenes) and $R^1$ ($R^1$=methyl, ethyl, alkyl) groups, said acetals have R (R=H, alkyl, aryl, heterocyclic and alkenes), $R^1$ ($R^1$=methyl, ethyl, alkyl) groups and $R^2$ ($R^2$=methyl, ethyl, alkyl) group
10. The method according to clauses 1-9 in which the aldehydes, ketones and alcohols is provided by first (i) providing alcohols; (ii) providing an oxidant (air, $H_2O_2$, $O_2$, NaOCl); (iii) optionally providing a catalyst which is heterogeneous supported metal catalyst, or a homogeneous organometallic complex, or a metal-free catalyst (mediator); and (iv) oxidizing enzyme (EC 1:10:3:2) oxidizing the alcohol, optionally in the presence of said catalyst.
then
   (v) providing aldehydes; or ketones (vi) providing a metal-free catalyst system (vii) optionally including an acid; or salt (vii) converting the aldehyde; or ketone, in the presence of said catalyst system or salt (viii) providing enals; or enones (ix) providing a reducing agent (formic acid, $H_2$, ammonium formiate, Hantzsch ester); (x) optionally providing a catalyst which is heterogeneous supported metal catalyst, or a homogeneous organometallic complex, or a metal-free catalyst; and (xi) reducing enzyme; reducing the enals; or enones, optionally in the presence of said catalyst. (xii) providing aldehydes; or ketones; or alcohols; or acetals.
11. The method according to clause 10 in which the condensation catalyst is an organocatalytic system or salt.

12. The method according to clause 10 wherein said alcohol-groups are primary alcohols, said aldehyde moiety has an R group (R=H, alkyl, aryl and heterocyclic).
13. The method according to clause 10 wherein said alcohol-groups are secondary alcohols, said keto-group have R (R=H, alkyl, aryl, heterocyclic and alkenes) and $R^1$ ($R^1$=methyl, ethyl and alkyl) groups.
14. The method according to clause 10 wherein said aldehydes are linear or branched aldehydes, said aldehyde moiety has an R group (R=H, alkyl, aryl and heterocyclic).
15. The method according to clause 10 wherein said enals are linear or branched aldehydes, said enal has an R group (R=H, alkyl, aryl and heterocyclic).
16. The method according to clause 10 wherein said ketones are linear or branched ketones, said ketone have R (R=H, alkyl, aryl, heterocyclic and alkenes) and $R^1$ ($R^1$=methyl, ethyl and alkyl) groups).
17. The method according to clause 10 wherein said enones are linear or branched enones, said enone have R (R=H, alkyl, aryl, heterocyclic and alkenes) and $R^1$ ($R^1$=methyl, ethyl and alkyl) groups).
18. The method according to clause 10 wherein said alcohols are methanol, ethanol, propanol, butanol, benzyl alcohols, isopropanol, hexanol, octanol, nonanol, hexadecanon and octadecanol.
19. The method according to clause 10 wherein said alcohols are derived from biomass.
20. The method according to clause 10 wherein said alcohols are derived from triglycerides.
21. The method according to clause 10 wherein said alcohols fatty acids.
22. The method according clause 10 wherein said alcohols are derived from wood.
23. The method according clause 10 wherein said alcohols are derived from fermentation.
24. The method according clause 10 wherein said alcohols are derived from wood.
25. The method according clause 10 wherein said alcohols are derived from algae.
26. The method according clause 10 wherein said alcohols are derived from fossil based material.
27. The method according clause 10 wherein said alcohols are derived from gasification.
28. The method according clause 10 wherein said alcohols are derived from pyrolysis.
29. The method according to clause 10 wherein said aldehydes are acetaldehyde, formaldehyde, propanal, butanal, pentanal, hexanal, octanal, 2,4-Hexadienal, cinnamic aldehydes and benzylic aldehydes.
30. The method according to clauses 1-9 in which the aldehyde, ketone, alcohol or acetal is provided by first (i) providing alcohols; (ii) providing an oxidant (air, O2, NaClO); (iii) optionally providing an oxidation catalysts system which is a Tempo, CuBr, bpy, NMI, $O_2$; or Tempo, $HNO_3$, HCl, $O_2$; or Tempo, NaOCl, KBr; or a heterogeneous supported metal catalyst (Pd, Ag, Ru, Ir, Fe); or a homogeneous catalyst system (Pd, Ag, Ru, Ir, Fe) and (iii) converting the alcohol; in the presence of said oxidation catalyst system.
then
(v) providing aldehydes; or ketones (vi) providing an amine catalyst system (vii) optionally including an acid; or salt (vii) converting the aldehyde; or ketone, in the presence of said catalyst system or salt (viii) providing enals; or enones (ix) providing a reducing agent (formic acid, H2, ammonium formiate); (x) optionally providing a catalyst which is heterogeneous supported metal catalyst (Pd, Ag, Ru, Ir, Fe, Ni, Co), or a homogeneous organometallic complex (Pd, Ag, Ru, Ir, Fe, Ni, Co); reducing the enals; or enones, optionally in the presence of said catalyst. (xii) providing aldehydes; or ketones; or alcohols; or acetals.

The invention claimed is:
1. A method for conversion of a starting alcohol being derived from any of biomass, triglycerides, wood, algae, fossil-based material, and syngas, or the starting alcohol is generated through any of fermentation and pyrolysis, or the starting alcohol is a fatty alcohol, comprising:
  (i) oxidizing the starting alcohol to a corresponding aldehyde or ketone, wherein the oxidizing is performed with an oxidant and a catalyst, the oxidant being any one of oxygen, air, hydrogen peroxide, and sodium hypochlorite, and the catalyst being any one of a heterogeneous supported metal catalyst, a homogeneous organometallic complex, a metal-free catalyst, and an enzyme;
  (ii) condensation of the corresponding aldehyde or ketone to an enal or enone using a metal-free condensation catalyst; and
  (iii) reducing, using a heterogeneous metal catalyst, and a reducing agent, the enal or enone to a product, said product being an alcohol, an aldehyde, a ketone, an acetal or a ketal, wherein the product has a longer chain than the chain of the starting alcohol;
wherein said method is performed in one-pot procedure without any purification of intermediates.
2. The method according to claim 1, wherein said starting alcohol is a primary alcohol of formula R—$CH_2$—OH, wherein R is a H, an alkyl, an aryl, an alkenyl, or a heterocyclic group.
3. The method according to claim 1, wherein said starting alcohol is a secondary alcohol of formula R—CH(OH)—$R^1$, wherein R is a H, an alkyl, an aryl, an alkenyl, or a heterocyclic group and $R^1$ is an alkyl.
4. The method according to claim 1, comprising repeating the steps of claim 1, using the product alcohol as the starting alcohol.
5. The method according to claim 1, wherein the condensation of aldehydes is performed with an organocatalyst or a salt thereof, and the catalyst is pyrrolidine, proline, ammonium formiate or glycine, optionally in the presence of an acid, selected from a group comprising acetic acid.
6. The method according to claim 1, wherein reducing is performed with a reduction agent, which is formic acid, $H_2$, ammonium formiate, or Hantzsch ester.
7. The method according to claim 1, comprising the steps of:
  (i) providing the starting alcohol,
  (ii) providing an oxidant, selected from a group comprising air, $H_2O_2$, $O_2$, or NaOCl,
  (iii) providing an oxidizing catalyst, selected from a group comprising a heterogeneous supported metal catalyst, or a homogeneous organometallic complex, or a metal-free catalyst (mediator), or an oxidizing enzyme (EC 1:10:3:2) and oxidizing the starting alcohol, in the presence of said oxidizing catalyst, into the corresponding aldehyde or ketone,
  (iv) providing a metal-free condensation catalyst system,
  (v) optionally including an acid or a salt thereof, and converting the corresponding aldehyde or ketone, in the presence of said condensation catalyst system, into the enal or enone,

(vi) providing a reducing agent, selected from a group comprising formic acid, $H_2$, ammonium formiate, or Hantzsch ester; and
(vii) providing a reducing catalyst, which is a heterogeneous metal catalyst and reducing the enal or enone, optionally in the presence of said reducing catalyst, into the product.

8. The method according to claim 7, wherein the condensation catalyst system is an organocatalytic system or a salt thereof.

9. The method according to claim 7, wherein said starting alcohol is selected from the group consisting of methanol, ethanol, propanol, butanol, benzyl alcohol, isopropanol, hexanol, octanol, nonanol and octadecanol.

10. The method according to claim 7, wherein said corresponding aldehyde is acetaldehyde, formaldehyde, propanal, butanal, pentanal, hexanal, octanal, 2,4-Hexadienal, cinnamic aldehyde or benzylic aldehyde.

11. The method according to claim 1, comprising:
(i) providing the starting alcohol,
(ii) providing an oxidant, selected from a group comprising air, $O_2$, or NaClO,
(iii) providing an oxidation catalysts system, selected from a group comprising TEMPO, CuBr, bpy, NMI, $O_2$; or TEMPO, $HNO_3$, HCl, $O_2$; or TEMPO, NaOCl, KBr; or a heterogeneous supported metal catalyst (Pd, Ag, Ru, Ir, or Fe); or a homogeneous catalyst system (Pd, Ag, Ru, Ir, or Fe) and converting the starting alcohol, in the presence of said oxidation catalyst system, into the corresponding aldehyde or ketone,
(iv) providing an amine catalyst system or a salt thereof,
(v) optionally including an acid, and converting the corresponding aldehyde or ketone, in the presence of said amine catalyst system or the salt thereof, optionally including an acid, into the enal or enone,
(vi) providing a reducing agent, selected from a group comprising formic acid, $H_2$, or ammonium formiate,
(vii) providing a reducing catalyst, which is a heterogeneous metal catalyst; and reducing the enal or enone, optionally in the presence of said reducing catalyst, into the product.

12. The method according to claim 1, wherein the method is performed in one-pot procedure without any purification of intermediates comprising:
providing the starting alcohol, which is a microwave-vial containing hexanol or octanol (1 mmol),
providing an oxidation catalysts system, which is TEMPO (1 mol %) in $CHCl_2$ (2.5 ml), which is sonicated for 3 minutes and cooled to 10° C. under stirring, where after cooled NaBr (10 mol %) and NaOCl (2.8 equiv.) is added and the pH adjusted to 9 by sat. $NaHCO_3$, and converting the starting alcohol into the corresponding aldehyde or ketone,
providing an oxidant, which is a balloon filled with $O_2$-gas at 10° C. under stirring for 10 minutes,
extracting the organic phase using $CHCl_2$ (3×5 ml) and drying of the reaction mixture over $Na_2SO_4$, evaporating the solvent and transferring the dry reaction mixture to a microwave-vial
adding toluene (0.5 ml) and pyrrolidine (5 mol %) and acetic acid (5 mol %) at 60° C. under stirring for 4 hours, and converting the corresponding aldehyde or ketone into the enal or enone,
cooling to room temperature,
adding a reducing catalyst and a reducing agent, which is a balloon filled with $H_2$ gas, and under stirring for 4 hours at room temperature and reducing the enal or enone into the product.

13. The method according to claim 1, wherein the method is performed in one-pot procedure without any purification of intermediates comprising:
providing the starting alcohol, which is a microwave-vial containing ethanol (1 mmol),
providing an oxidation catalysts system, which is TEMPO (1 mol %) in $CHCl_2$ (2.5 ml), which is sonificated for 3 minutes and cooled to 10° C. under stirring, where after cooled NaBr (10 mol %) and NaOCl (2.8 equiv.) is added and the pH adjusted to 9 by sat. $NaHCO_3$,
providing an oxidant, which is a balloon filled with $O_2$-gas at 10° C. under stirring for 3 hours, and converting the starting alcohol into the corresponding aldehyde or ketone,
adding toluene (0.5 ml) and pyrrolidine (5 mol %) and acetic acid (5 mol %) at room temperature under stirring for 3 hours, and converting the corresponding aldehyde or ketone into the enal or enone,
cooling to room temperature,
adding a reducing catalyst and a reducing agent, which is a balloon filled with $H_2$ gas, and under stirring for 3 hours at room temperature and reducing the enal or enone into the product.

14. The method according to claim 1, wherein the method is performed in a sequential procedure.

* * * * *